# United States Patent [19]

Kummer et al.

[11] 4,310,686

[45] Jan. 12, 1982

[54] PREPARATION OF BUTANEDICARBOXYLIC ESTERS

[75] Inventors: Rudolf Kummer, Frankenthal; Heinz-Walter Schneider; Volker Taglieber, both of Ludwigshafen; Franz-Josef Weiss, Weinheim, all of Fed. Rep. of Germany

[73] Assignee: BASF Aktiengesellschaft, Fed. Rep. of Germany

[21] Appl. No.: 153,572

[22] Filed: May 27, 1980

[30] Foreign Application Priority Data

Jun. 20, 1979 [DE] Fed. Rep. of Germany ....... 2924785

[51] Int. Cl.$^3$ .............................................. C07C 67/38
[52] U.S. Cl. .................................... 560/204; 252/414
[58] Field of Search ......................... 560/204; 252/414

[56] References Cited

U.S. PATENT DOCUMENTS

| 2,542,767 | 2/1951 | Gresham et al. | 560/204 |
| 3,507,891 | 4/1970 | Hearne et al. | 560/204 |
| 3,778,466 | 12/1973 | Matsuda | 560/204 |
| 3,856,832 | 12/1974 | Ethyl Corp. | 560/204 |
| 4,041,057 | 8/1977 | Fanning | 560/204 |
| 4,169,956 | 10/1979 | Kummer et al. | 560/204 |
| 4,171,451 | 10/1979 | Kummer et al. | 560/204 |

FOREIGN PATENT DOCUMENTS 2159139 6/1972 Fed. Rep. of Germany .
2741511 3/1979 Fed. Rep. of Germany .

OTHER PUBLICATIONS

Bull. Chem. Soc. Japan 46, pp. 524–530, (1973).

*Primary Examiner*—Natalie Trousof
*Assistant Examiner*—Vera C. Clarke

*Attorney, Agent, or Firm*—Keil & Witherspoon

[57] ABSTRACT

A process for the preparation of butanedicarboxylic acid esters, wherein (a) an aqueous cobalt salt solution is treated with excess carbon monoxide and hydrogen in the presence of active charcoal laden with cobalt carbonyl, (b) the resulting aqueous solution of cobalt carbonyl hydride is extracted with butadiene or a butadiene containing hydrocarbon mixture and the aqueous phase is separated off, (c) the butadiene, or butadiene/hydrocarbon mixture, containing cobalt carbonyl hydride, cobalt carbonyl and butenyl-cobalt tricarbonyl, is reacted with carbon monoxide and excess $C_1$–$C_4$-alkanol in the presence of a tertiary nitrogen base, (d) the resulting reaction mixture is freed from the tertiary nitrogen base contained therein, down to a content of from 0.1 to 0.3 mole per mole of pentenoic acid ester, and from excess hydrocarbons, and the pentenoic acid ester remaining in the reaction mixture is reacted with carbon monoxide and excess $C_1$–$C_4$-alkanol in the presence of the cobalt carbonyl and tertiary nitrogen base contained in the reaction mixture, (e) the reaction mixture is treated with an oxidizing agent in the presence of the aqueous acid solution which has been separated off in stage (b), and the mixture is separated into an organic phase, from which butanedicarboxylic acid esters are isolated by distillation, and an aqueous phase, and (f) the aqueous phase is extracted with water-immiscible solvents, the phases are separated, and the resulting aqueous phase is freed from alkanols and tertiary nitrogen base and is recycled to stage (a).

6 Claims, No Drawings

PREPARATION OF BUTANEDICARBOXYLIC ESTERS

The present invention relates to a process for the preparation of butanedicarboxylic acid esters, wherein butadiene or a butadiene-containing hydrocarbon mixture is reacted with carbon monoxide and a lower alcohol in the presence of a tertiary nitrogen base and cobalt carbonyl at from 80° to 150° C. under superatmospheric pressure and the resulting pentenoic acid ester is further reacted with carbon monoxide and lower alcohol at from 140° to 200° C. under superatmospheric pressure, to give butanedicarboxylic acid esters.

Bull. Chem. Soc. Japan 46 (1973), 524 et seq. discloses a two-stage process for the preparation of adipic acid esters from butadiene, wherein butadiene is first reacted with carbon monoxide and an alkanol in the presence of cobalt carbonyl and a nitrogen base, eg. pyridine or isoquinoline, and, without removing the catalyst, the pentenoic acid ester formed is further reacted, in a subsequent stage, with carbon monoxide and alkanol to give adipic acid. However, in carrying out such a process industrially it is necessary to recover and recycle the catalyst. Thus, in the process disclosed in U.S. Pat. No. 3,778,466, the catalyst-containing residue obtained after distilling off the useful products is reused for the carbonylation. However, it has been found that after, for example, using the catalyst 4 times, its activity drops considerably. This is attributable to the fact, on the one hand, that the distillation damages the catalyst, since cobalt carbonyl complexes are not heat-stable, whilst on the other hand the carbonylation produces by-products which influence the carbonylation and must therefore be removed continuously. Attempts have also already been made to separate, after carbonylation, the useful products from the catalyst-containing residue by extraction. Thus, German Laid-Open Application DOS No. 2,159,139 describes a process wherein the methanol-containing carbonylation mixture is extracted with hydrocarbons. It is true that in this way it proves possible to separate off the useful products without damaging the catalyst, and to recycle a methanolic catalyst-containing solution to the carbonylation. However, this extractive separation is not a suitable method of removing by-products such as polymeric butadienes, which are formed during the carbonylation. Hence, these accumulate progressively if the catalyst solution is repeatedly re-used, and then interfere with the carbonylation. According to German Laid-Open Application DOS No. 2,741,511, hydrocarbons, ketones or ethers are used as extractant of the catalyst stream, which is thereby converted to an aqueous solution. Apart from the fact that an extraction column with a large number of separation stages is necessary, it does not prove possible to remove the by-products to the degree required for trouble-free operation of the reaction.

It is an object of the present invention to treat the aqueous cobalt salt solution which is to be recycled, in such a way that the carbonylation proves trouble-free and in addition the extraction is simplified.

We have found that this object is achieved by a process for the preparation of butanedicarboxylic acid esters by reacting butadiene or a butadiene-containing hydrocarbon mixture with carbon monoxide and $C_1$-$C_4$-alkanol in the presence of a tertiary nitrogen base and a cobalt carbonyl at from 80° to 150° C. under superatmospheric pressure and, without removing the catalyst, then reacting the pentenoic acid ester obtained with carbon monoxide and $C_1$-$C_4$-alkanol at from 140° to 200° C. under superatmospheric pressure, to give butanedicarboxylic acid esters, comprising the steps that (a) an aqueous cobalt salt solution is treated, at from 50° to 200° C. and under a pressure of from 50 to 500 bar, with excess carbon monoxide and hydrogen in the presence of active charcoal which has been laden with cobalt carbonyl, (b) the resulting aqueous solution of cobalt carbonyl hydride is extracted with butadiene or a butadiene-containing hydrocarbon mixture and the aqueous phase is separated off, (c) the butadiene, or butadiene/hydrocarbon mixture, containing cobalt carbonyl hydride, cobalt carbonyl and butenyl-cobalt tricarbonyl, is reacted with carbon monoxide and excess $C_1$-$C_4$-alkanol in the presence of from 0.5 to 2 moles, per mole of butadiene, of a tertiary nitrogen base having a $pK_a$ of from 3 to 11, at from 80° to 150° under a pressure of from 300 to 2,000 bar, (d) the resulting reaction mixture is freed from the tertiary nitrogen base contained therein, down to a content of from 0.1 to 0.3 mole per mole of pentenoic acid ester, and from excess hydrocarbons, and the pentenoic acid ester remaining in the reaction mixture is reacted with carbon monoxide and excess $C_1$-$C_4$-alkanol at from 140° to 200° C. and under a pressure of from 100 to 400 bar in the presence of the amounts of cobalt carbonyl and tertiary nitrogen base contained in the reaction mixture, (e) the reaction mixture containing cobalt carbonyl, alkanols, nitrogen base, butanedicarboxylic acid esters, by-products and unconverted pentenoic acid esters is treated with an oxidizing agent in the presence of the aqueous acid solution which has been separated off in stage (b), and the mixture is separated into an organic phase, from which butanedicarboxylic acid esters are isolated by distillation, and an aqueus phase, and (f) the aqueous phase is extracted with water-immiscible solvents, the phases are separated and the aqueous phase thus obtained is freed from alkanols and tertiary nitrogen base by distilling these off, and is recycled to stage (a), wherein the extractant used in stage (f) consists of $C_1$-$C_4$-alkyl esters of $C_1$-$C_5$-alkanecarboxylic acids and/or alkenecarboxylic acids.

The novel process has the advantage that fewer extraction stages are needed and that substantially smaller amounts of extractant need be employed. In addition, the novel process has the advantage that in particular, by-products which damage the catalyst are removed more completely than hitherto. Finally, the novel process has the advantage that if alkyl pentanoates or alkyl penetenoates are used, products which are formed per se during the process of preparation are used as extractants and it is not necessary to employ extractants of a different nature to materials present in the synthesis.

In a first stage (stage a), an aqueous cobalt salt solution is treated, at from 50° to 200° C. and under a pressure of from 50 to 500 bar, with excess carbon monoxide and excess hydrogen in the presence of active charcoal which has been laden with cobalt carbonyl. Preferably, the cobalt salts used are fatty acid salts which are water-soluble, especially formates, acetates, propionates and butyrates. Cobalt formate and cobalt acetate have proved particularly suitable. It is advantageous to start from a solution which contains from 0.5 to 5% by weight of cobalt, calculated as metal, in particular from 1 to 3% by weight of cobalt, the cobalt being in the form of the above salts. In general, the gas mixture employed contains carbon monoxide and hydrogen in a volume ratio of from 4:1 to 1:2, especially from 2:1 to 1:1. An about equimolecular mixture of carbon monoxide and hydrogen has provided particularly suitable. Advantageously, the mixture of carbon monoxide and hydrogen is employed in excess, for example in up to 5 times the stoichiometric amount. Further advantageous conditions are 100°-170° C. and a pressure of from 100 to 400 bar.

The treatment in stage a is carried out in the presence of active charcoal. Examples of suitable types of active charcoal are peat charcoal, animal charcoal and sugar charcoal, the first-mentioned being particularly suitable. Advantageously, the active charcoal is laden to saturation with cobalt carbonyl; this is generally achieved by passing an aqueous solution of a cobalt salt, together with the above gas mixture of carbon monoxide and hydrogen, over the active charcoal, under the stated reaction conditions, until the charcoal is saturated, ie. until cobalt carbonyl and cobalt carbonyl hydride are analytically detectable in the mixture which issues.

In general, the treatment is carried out in a treatment zone which advantageously has a length:diameter ratio of from 5:1 to 50:1 and in which the active charcoal is as a rule arranged as a fixed bed. Advantageously, the hourly throughput is from 1.5 to 15 g of cobalt, calculated as metal, in the form of one of the above salts, per kilogram of active charcoal.

The resulting aqueous solution, containing cobalt carbonyl hydride, unconverted cobalt salts and liberated acid, is fed, advantageously together with the unconsumed mixture of carbon monoxide and hydrogen, and advantageously without releasing the pressure, to the second stage (stage b). There, cobalt carbonyl hydride is extracted with butadiene or a butadiene-containing hydrocarbon mixture, such mixtures being discussed in more detail later. It is possible to carry out the extraction with all or only a part of the amount of butadiene required for the carbonylation; advantageously, from 50 to 30 moles of butadiene are employed per gram atom of cobalt to be extracted. The extraction is carried out in counter-current or co-current, in apparatus conventionally used for industrial extractions, for example columns or static mixers. During the extraction, the system is kept at 20°-100° C. and a pressure of from 5 to 300 bar. The mixture is subsequently separated into an aqueous phase and an organic phase. If, for example, the extraction is carried out in a pressure tube filled with Raschig rings, separation into an organic phase and an aqueous phase occurs simultaneously, in the upper part of the tube. At the same time, the mixture of carbon monoxide and hydrogen used is separated off as a gaseous phase. The cobalt content of the organic phase leaving stage b is in general from 1 to 5% by weight. It is assumed that the cobalt carbonyl is present in the organic phase as a water-insoluble complex with butadiene.

The organic phase is then reacted, in stage c, with excess $C_1$-$C_4$-alkanol at from 80° to 150° C. under a pressure of from 300 to 2,000 bar, in the presence of from 0.5 to 2 moles of tertiary nitrogen base, having a $pK_a$ of from 3 to 11, per mole of butadiene, with the proviso that the tertiary nitrogen base should preferably be lower-boiling than the pentenoic acid ester to be produced.

If not the entire amount of butadiene or butadiene-containing hydrocarbon mixture required for the carbonylation was used for the extraction, the requisite additional amount of starting materials is introduced into stage (c). It should be noted that butadiene-containing hydrocarbon mixtures can advantageously be used in place of pure butadiene. Such hydrocarbon mixtures contain butadiene together with saturated hydrocarbons of 3 to 5 carbon atoms and mono-unsaturated olefins of 3 to 5 carbon atoms. In industrial operation, the starting mixtures used are in particular $C_4$ cuts which are obtained on dehydrogenation of butane or butene, or obtained as by-products of the production of ethylene by thermal cracking of light gasoline or of higher hydrocarbon cuts. Such mixtures as a rule contain from 40 to 60% by weight of butadiene, from 20 to 35% by weight of isobutene, from 10 to 25% by weight of but-1-ene, from 5 to 15% by weight of but-2-ene, from 1 to 10% by weight of butanes and from 0.1 to 3% by weight of butynes.

Preferred tertiary nitrogen bases are N-heterocyclic compounds, such as pyridine ($pK_a$ 5.3), methylpyridines, eg. 3-picoline ($pK_a$ 6.0) and isoquinoline ($pK_a$ 5.4); pyridine is industrially of particular importance. It has proved especially advantageous to use from 0.6 to 1.5 moles of tertiary nitrogen base per mole of butadiene.

Suitable $C_1$-$C_4$-alkanols are methanol, ethanol, propanol, butanol and isobutanol; the first-mentioned is particularly preferred.

The reaction is preferably carried out at from 120° to 140° C. under a pressure of from 600 to 1,200 bar. Per mole of butadiene, from 0.01 to 0.1 gram atom of cobalt, in the form of the carbonyl complexes which have been described, is as a rule employed.

In addition to unconverted butadiene, with or without other hydrocarbons, the reaction mixture obtained contains tertiary nitrogen base, cobalt carbonyl complexes, unconverted alkanol, the pentenoic acid esters obtained as the useful products, and by-products such as valeric acid esters, vinylcyclohexene, butenyl ketones, butyl ketones and butadiene polymers.

After letting down the pressure, the tertiary nitrogen base contained in this reaction mixture is removed down to a content of from 0.1 to 0.3 mole per mole of pentenoic acid ester, and any excess hydrocarbons are also removed (stage d). This separation can be effected by distillation or by other methods, eg. extraction. Advantageously, tertiary nitrogen base and any excess hydrocarbons are removed by distillation under reduced pressure; during this distillation, the bottom temperature should not exceed 75° C., to avoid decomposing the cobalt catalyst. Depending on the particular alkanol used, part or all of the excess alkanol distils off at the same time.

The pentenoic acid ester which remains in the reaction mixture is reacted with carbon monoxide and excess $C_1$-$C_4$-alkanol (after an appropriate amount of alkanol has, if necessary, again been added), at from 140° to 200° C. under a pressure of from 100 to 400 bar, in the presence of the amount of cobalt catalyst and tertiary nitrogen base already contained in the reaction mixture, advantageously at from 150° to 180° C. Preferably, the amount of alkanol present is from 1.5 to 4 moles per mole of pentenoic acid ester. It has also proved advantageous to add a few, for example from 1 to 4, percent by volume of hydrogen to the carbon monoxide.

The reaction mixture containing catalyst, butanedicarboxylic acid esters, alkanols, tertiary nitrogen base, pentenoic acid esters and by-products is treated, in stage (e), with an oxidizing agent in an aqueous acid medium. Particularly suitable oxidizing agents are those which do not contaminate the reaction mixture, for example hydrogen peroxide, oxygen or an oxygen-containing gas. Gases containing molecular oxygen, especially air, are particularly preferred. The oxidizing agent is used in an amount of at least two oxidation equivalents per mole of cobalt compound. Preferably, however, an excess is used; in practice, it has proved advantageous to employ from 30 to 300 liters (S.T.P.) of air per kilogram of reaction mixture.

In general, from 0.1 to 10, advantageously from 0.2 to 1, part by weight of water is used per part by weight of reaction mixture. The pH is advantageously from 3 to 6. The aqueous acid solution obtained after removing the butadiene, containing cobalt carbonyl hydride, from the mixture obtained in stage (b) constitutes a suitable acid medium. Such an acid solution for example contains, if cobalt acetate has been used initially, acetic acid together with unconverted cobalt acetate. Where necessary, a suitable fatty acid may additionally be introduced. It is essential to ensure that sufficient acid is present to keep the cobalt salt in solution. Similar remarks apply to the amount of water to be used. In order that the cobalt solution should not be excessively dilute it is advantageous to recycle the aqueous cobalt-containing solution to the treatment zone and only separate off a small part-stream, corresponding to the amount introduced.

The treatment is advantageously carried out at from 80° to 160° C., especially at from 100° to 130° C. Depending on the degree of mixing, the reaction may be complete after only a few seconds and in many cases after only a fraction of a second. To ensure good mixing it is for example advantageous to feed the reaction mixture in a finely divided form into the aqueous acid solution, whilst at the same time feeding in the oxidizing agent.

After the treatment the liquid phase is separated, for example by decanting, into an organic phase and an aqueous phase. Fractional distillation of the organic phase gives unconverted pentenoic acid ester, which can be recycled to the carbonylation, as well as valeric acid ester and a mixture of butanedicarboxylic acid esters. The ester mixture can be used to prepare diols or polyesters. The adipic acid ester obtained from the ester mixture by fractional distillation may be used for the preparation of adipic acid, AH salt, adipodinitrile and hexane-1,6-diol.

The aqueous phase, containing cobalt salts, with or without some free acid, as well as alkanols and tertiary nitrogen base, is extracted, in stage f, with water-immiscible solvents, before being recycled into stage a to serve as starting solution for the preparation of cobalt carbonyl hydride. According to the invention, the extractants used in stage (f) are $C_1$-$C_4$-alkyl esters of $C_1$-$C_5$-alkanecarboxylic acids and/or alkenecarboxylic acids. Esters boiling above 65° C. have proved particularly suitable. $C_1$-$C_4$-alkyl esters of $C_4$-$C_5$-alkanecarboxylic acids and/or alkenecarboxylic acids, especially valeric acid esters and pentenoic acid esters, are particularly important for industrial purposes. The preferred method, for industrial purposes, is to use alkyl esters of valeric acid and/or of pentenoic acid, which are formed in the process according to the invention, as extractants.

The extraction may be carried out by any conventional industrial procedure, for example co-current extraction and counter-current extraction, and in any conventional industrial apparatus, for example pulse columns, static mixers and mixer-settlers. As a rule, the extraction is carried out at the temperature at which the aqueous phase is obtained after separating off the organic phase, for example at from 20° to 60° C. As a rule, from 0.05 to 1 part by volume, especially from 0.1 to 0.3 part by volume, of the said alkyl esters of alkanecarboxylic acids and/or alkenecarboxylic acids is used per part by volume of aqueous solution containing cobalt salts.

After the extraction, the aqueous solution is freed from alkanol and nitrogen base by distillation and is re-used, as already described, for the preparation of catalyst solution in stage (a). The organic phase resulting from the extraction is advantageously fed to the reaction mixture in stage (e) after the oxidative treatment. This facilitates phase separation and additionally recycles extracted butanedicarboxylic acid esters, so that separate working up is not necessary. The alkyl esters of alkanoic acids or alkenoic acids obtained on working up the organic phase are re-used for the extraction.

An advantageous procedure is to distil off valeric acid esters, mixed with pentenoic acid esters, as a low-boiling azeotrope with water and/or azeotrope with water and pyridine, from the organic phase after the phase separation in stage (e), and use the azeotrope as a two-phase mixture for the extraction. To carry out this distillation, water and pyridine, in an amount corresponding to the composition of the azeotrope and to the desired amount of extractant, are run into the extractant column, in addition to the organic phase. The pyridine-water mixture which is in this way additionally introduced into the aqueous phase of the extraction is recovered on working up the aqueous phase after separating off the alkanol, and can be recycled to the feed of the extractant column in stage (e). Extraction using a binary and/or ternary alkyl valerate azeotrope and/or alkyl pentenoate azeotrope does not differ, in its result, from the result of carrying out the extraction with pure alkyl valerates or alkyl pentenoates.

The Examples which follow illustrate the process according to the invention.

EXAMPLE 1

A high pressure tube which is filled with 600 ml of active charcoal (particle size 3–5 mm, from Norit) is charged with 180 ml per hour of an aqueous cobalt acetate solution which contains 2.5% by weight of cobalt$^{2+}$. The above solution is obtained as the aqueous phase in stage (e). In addition, 50 liters (S.T.P.) per hour of an equimolar mixture of carbon monoxide and hydrogen are introduced into the tube. The conditions maintained are 120° C. and a presure of 300 bar. The solution taken off in the lower part of the tube contains 0.65% by weight of cobalt$^{2+}$ and 1.85% by weight of cobalt in the form of cobalt carbonyl hydride, as well as the corresponding amount of acetic acid. This solution is let down to 20 bar and then thoroughly mixed, at room temperature, with 310 ml of a $C_4$ cut which contains 43% by weight of butadiene (1.57 moles). After the phase separation, the $C_4$ cut contains 3.7 g of cobalt in the form of cobalt carbonyl compounds. This cobalt-containing C$_4$ cut is then fed to a high-pressure vessel of 1.9 liters capacity, and in addition 127 ml (1.57 moles) of pyridine, 127 ml (3.14 moles) of methanol and 60 liters (S.T.P.) of carbon monoxide are introduced per hour. The carbonylation takes place at 130° C. and 600 bar. The product taken off at the top of the high-pressure vessel is let down, thereby separating off excess C$_4$ hydrocarbons, in the gaseous form, in addition to excess carbon monoxide. These hydrocarbons contain virtually no butadiene. Per hour, about 52 g of methanol and 100 g of pyridine are distilled from the discharged material, the distillation being carried out under reduced pressure so as not to damage the catalyst. The bottom temperature is restricted to a maximum of 65° C. The bottom material, which contains 3.7 g of cobalt as a carbonyl complex and 165 g (1.44 moles) of pentenoic acid esters is fed, together with 117 ml (2.88 moles) of methanol and 55 liters (S.T.P.) of carbon monoxide, containing 2% by volume of hydrogen, continuously from below into an additional high-pressure vessel, of 1.7 liters capacity. The carbonylation is carried out at 170° C. under a pressure of 150 bar. The material discharged from the reaction is thoroughly mixed with 200 ml per hour of the aqueous solution obtained from extraction stage (b), in a tube packed with Raschig rings, whilst passing about 200 liters (S.T.P.) per hour of air at 100° C. through the tube.

After the phase separation, the organic phase, together with 50 ml of a pyridine-water mixture (containing about 50% of pyridine) originating from the working up of the aqueous phase, is fed to a distillation column. The material discharged from the bottom, which prinicipally consists of pyridine, methyl valerate, methyl pentenoate and methyl butanedicarboxylate, is subjected to fractional distillation. The two-phase material obtained at the top (at 100 ml per hour) consists of about 40% of methyl valerate, about 10% of methyl pentenoate and about 25% each of pyridine and water, and is pumped directly into a counter-current pulse column of 1.5 m length and 30 mm diameter. After the extraction, the aqueus phase no longer contains any butanedicarboxylic acid ester and, after methanol and pyridine have conjointly been distilled off (as an azeotrope with water), is recycled, as a 2.5% strength cobalt acetate solution, into stage a) at the rate of 200 ml per hour. In a further distillation, 30 ml of methanol as top product and 90 ml of pyridine-water mixture as bottom product are obtained per hour. 50 ml per hour of the pyridine-water mixture are recycled to the extractant column and the remaining 40 ml, as well as the organic phase from the extraction, are recycled to the product stream, upstream of the phase separation.

COMPARATIVE EXAMPLE

The procedure followed is as in Example 1, except that the extraction is carried out with 50 ml per hour of cyclohexane instead of the methyl valerate/methyl pentenoate mixture, and the pyridine-water mixture obtained on working up the aqueous phase is completely recycled to the product stream, upstream of the phase separation.

After extraction, the aqueous phase still contains 0.4% of dimethyl butanedicarboxylates. Partial hydrolysis of these esters in the course of the formation of the catalyst in stage (a) results, after only 4 cycles, in a content of 0.6% of monomethyl butanedicarboxylates and about 0.8% of butanedicarboxylic acids. Consequently, sparingly soluble cobalt pyridine adipates and methylglutarates precipitate, causing pipeline blockages and catalyst losses.

We claim:
1. A process for the preparation of butanedicarboxylic acid esters, wherein
   (a) an aqueous cobalt salt solution is treated, at from 50° to 200° C. and under a pressure of from 50 to 500 bar, with excess carbon monoxide and hydrogen in the presence of active charcoal which has been laden with cobalt carbonyl,
   (b) the resulting aqueous solution of cobalt carbonyl hydride is extracted with butadiene or a butadiene-containing hydrocarbon mixture and the aqueous phase is separated off,
   (c) the butadiene, or butadiene/hydrocarbon mixture, containing cobalt carbonyl hydride, cobalt carbonyl and butenyl-cobalt tricarbonyl, is reacted with carbon monoxide and excess C$_1$-C$_4$-alkanol in the presence of from 0.5 to 2 moles, per mole of butadiene, of a tertiary nitrogen base having a pK$_a$ of from 3 to 11, at from 80° to 150° C. under a pressure of from 300 to 2,000 bar,
   (d) the resulting reaction mixture is freed from the tertiary nitrogen base contained therein, down to a content of from 0.1 to 0.3 mole per mole of pentenoic acid ester, and from excess hydrocarbons, and the pentenoic acid ester remaining in the reaction mixture is reacted with carbon monoxide and excess C$_1$-C$_4$-alkanol at from 140° to 200° C. and under a pressure of from 100 to 400 bar in the presence of the amounts of cobalt carbonyl and tertiary nitrogen base contained in the reaction mixture,
   (e) the reaction mixture containing cobalt catalyst, butanedicarboxylic acid esters, alkanols, tertiary nitrogen base, pentenoic acid esters and by-products is treated with an oxidizing agent in the presence of the aqueous acid solution which has been separated off in stage (b), and the mixture is separated into an organic phase, from which butanedicarboxylic acid esters are isolated by distillation, and an aqueous phase, and (f) the aqueous phase is extracted with C$_1$-C$_4$-alkyl esters of C$_1$-C$_5$-alkanecarboxylic acids or C$_1$-C$_4$-alkyl esters of C$_4$-C$_5$-alkenecarboxylic acids or mixtures of said alkyl esters of alkanecarboxylic acids and alkyl esters of alkenecarboxylic acids, the phases are separated, and the aqueous phase thus obtained is freed from alkanols and tertiary nitrogen base by distilling these off and is recycled to stage (a).

2. The process of claim 1, wherein C$_1$-C$_4$-alkyl esters of C$_4$-C$_5$-alkanecarboxylic acids or C$_1$-C$_4$-alkyl esters of C$_4$-C$_5$-alkenecarboxylic acids or mixtures of these esters of alkanecarboxylic acids and alkyl esters of alkenecarboxylic acids are used as the extractant in step (f).

3. The process of claim 1, wherein the alkyl valerate or the alkyl pentenoate or a mixture of the alkyl valerate and alkyl pentenoate obtained as a by-product is used as the extractant in step (f).

4. The process of claim 1, wherein the alkyl ester extractant step (f) is alkyl valerate in the form of a binary azeotrope with water, or is alkyl valerate in the form of a ternary azeotrope of alkyl valerate with water and pyridine.

5. The process of claim 1, wherein the alkyl ester extractant of step (f) is methyl pentenoate in the form of a binary azeotrope of methyl pentenoate with water, or the extractant is methyl pentenoate in the form of a ternary azeotrope of methyl pentenoate with water and pyridine.

6. The process of claim 1, wherein the organic phase obtained after the extraction in stage (f) is recycled to stage (e) after the oxidative treatment.

* * * * *